United States Patent
Friedman

(10) Patent No.: US 6,586,195 B1
(45) Date of Patent: Jul. 1, 2003

(54) METHOD OF DETECTING SUGARS

(75) Inventor: Arthur J. Friedman, Deerfield, IL (US)

(73) Assignee: R.E. Davis Chemical Corporation, Oak Brook, IL (US)

( * ) Notice: Subject to any disclaimer, the term of this patent is extended or adjusted under 35 U.S.C. 154(b) by 82 days.

(21) Appl. No.: 10/015,216

(22) Filed: Nov. 19, 2001

(51) Int. Cl.$^7$ .............. C12Q 1/34; C12Q 1/54; C12Q 1/00; C12Q 3/00
(52) U.S. Cl. .............. 435/18; 435/14; 435/4; 435/967; 435/3
(58) Field of Search .............. 435/18, 14, 4, 435/967, 3

(56) References Cited

U.S. PATENT DOCUMENTS

| | | | |
|---|---|---|---|
| 3,164,534 A | 1/1965 | Free | 195/103.5 |
| 3,212,855 A | 10/1965 | Mast et al. | 23/253 |
| 3,367,842 A | 2/1968 | Rupe et al. | 195/103.5 |
| 3,384,554 A | 5/1968 | Martin | 195/103.5 |
| 3,477,817 A | 11/1969 | DeFalco | 23/230 |
| 3,721,607 A | 3/1973 | Gruber et al. | 195/103.5 |
| 3,791,988 A | 2/1974 | Josef et al. | 252/408 |
| 3,964,871 A | 6/1976 | Hochstrasser | 23/230 |
| 4,046,514 A | 9/1977 | Johnston et al. | 23/253 |
| 4,260,680 A | 4/1981 | Muramatsu et al. | 435/14 |
| 4,298,688 A | 11/1981 | Kallies | 435/14 |
| 4,477,314 A | 10/1984 | Richter et al. | 204/1 |
| 4,683,198 A | * 7/1987 | Ishikawa et al. | 435/22 |
| 4,748,114 A | 5/1988 | Kallies et al. | 435/14 |
| 5,550,032 A | 8/1996 | Isbister | 435/39 |
| 5,620,863 A | 4/1997 | Tomasco et al. | 435/14 |
| 5,866,349 A | 2/1999 | Lilja et al. | 435/13 |
| 6,027,692 A | * 2/2000 | Galen et al. | 422/82.05 |
| 6,063,637 A | * 5/2000 | Arnold et al. | 436/94 |

OTHER PUBLICATIONS

Kinetics—Early and Often, J.A., Campbell; Journal of Chemical Education, Nov. 1963, vol. 40, No. 11, pp 578–583.

Spot Tests in Organic Analysis, Fritz Feigl; 7th edition 1966; Elsevier Publishing Company; Amsterdam, London and New York; pp 337–341493.

Chemical Analysis—A Series of Monographs on Analytical Chemistry and its Applications, Ervin Jungreis; Second Edition, vol. 141, 1997, Wiley–Interscience Publication; new York, Chichester, Brisbane, Toronto, Singapore, Weinheim; p. 61.

* cited by examiner

*Primary Examiner*—Louise N. Leary
(74) *Attorney, Agent, or Firm*—Godfrey & Kahn, S.C.

(57) ABSTRACT

A method for detecting reducing sugars in samples using a test reagent containing an indicator capable of producing calorimetric changes when contacted with reducing sugars. Under alkaline conditions, reducing sugars present in a sample affect a reduction of the indicator to a colorless or differently colored reduced form. The method may include the additional step of pretreating the sample with a glycosidase to convert non-reducing sugars to reducing sugars.

10 Claims, No Drawings

METHOD OF DETECTING SUGARS

BACKGROUND OF THE INVENTION

The present invention relates generally to an analytical method, and more particularly to a simple and rapid method for the detection of sugars in food and beverage items.

Diabetes is a major health issue in the United States. In fact, diabetes mellitus, the most prevalent form of diabetes, is the fourth most common reason for patient contact with a physician and is a major cause of premature disability and mortality. It is the leading cause of blindness among working-age people, of end-stage renal disease, and of non-traumatic limb amputations. It increases the risk of cardiac, cerebral, and peripheral vascular disease two- to seven-fold and is a major cause of neonatal morbidity and mortality.

Personal factors promoting diabetes are well known. Increased age, reduced physical activity, and especially obesity promote diabetic conditions. In particular, severe and prolonged obesity is understood to substantially enhance the risk of the disease. However, medical data now indicate that most of the debilitating complications of the disease can be prevented or delayed by prospective treatment of the above-mentioned risk factors. For most diabetic individuals, particularly those having Type II diabetes, diet and exercise are the key intervention required to restore metabolic control. In this regard, it is desirable for diabetic individuals, or those at risk of diabetes, to carefully monitor their diet as modest maintenance of a low sugar diet often leads to substantial reductions in diabetic symptoms. In addition, individuals suffering from Type I diabetes, an often more severe condition than Type II, must rely on exogenous sources of insulin due to an absent or reduced insulin secretion ability. Departures from a consistent diet require active adjustment of insulin dosages and increase the chances of dangerous, health-threatening mistakes in dosage delivery.

In light of the above, a simple and rapid method useful in determining the presence of sugars in food and beverage items is desirable for individuals who must closely monitor their carbohydrate intake. Specifically, a method efficient at providing a quick and clear indication of the presence of sugars in food and beverage items would be found useful and welcomed by a multitude of diabetic individuals. In addition, those with a general interest in weight loss, a popular pursuit in our current society, would also find such a method useful. Also, food manufacturers, distributors and retailers would have a great interest in a convenient method for monitoring the sugar content of their respective food products, especially those offered to the public as diet or low-calorie items.

A method useful for fulfilling the requirements highlighted above would ideally be in kit format allowing a user to conveniently carry out the method at any time without the need for complex manipulations and apparatus. In the case of test reagents useful in a kit format, it is generally desired that the reagents contain all necessary components in a pre-mixed state in order to reduce as much as possible the opportunity for errors arising from mixing of several components. Test reagents should also remain stable for as long as possible to avoid having to prepare new solutions continuously. Unfortunately, previously known methods did not fulfill these requirements. For example, enzymatic determination of glucose by use of the enzymes glucose oxidase and peroxidase requires the continual preparation of new enzymatic reagents as the enzyme components are unstable for long periods of time once diluted in a working test reagent. Obviously, this method is not convenient for those interested in a quick and convenient determination of sugar content in a snack or meal. Likewise, chemical indicators, particularly methylene blue, are subject to rapid photodegradation thereby making long term storage and use of such test reagents by consumers all but impossible.

SUMMARY OF THE INVENTION

Therefore, it is an object of the present invention to provide a simple, rapid and relatively low priced method of detecting sugars in a liquid sample. The method includes an initial step of selecting an indicator capable of producing a colorimetric change when contacted with a reducing sugar. Indicators suitable for use in the invention are selected from the phenazine class of compounds and include azocarmine B, indoine blue, methylene violet 3RAX, safranine O, phenosafronin, and Janus Green B. Once selected, the indicator is preferably dissolved or diluted in water to form an aqueous solution and the pH of the aqueous solution is adjusted to be alkaline by the addition of a base, such as NaOH, KOH, $Sr(OH)_2$, $Ba(OH)_2$, and $NH_4OH$. Thusly prepared, the aqueous test reagent is particularly resistant to photodegradation and stable for long periods of time thereby eliminating the need to continually prepare fresh test reagent.

Subsequent to preparation, the method according to the present invention calls for the test reagent to be brought into contact with a sample. Reducing sugars, if present in the sample, cause the indicator in the test reagent to undergo a calorimetric change. Preferably, this calorimetric change is clearly visible to the naked eye of the user and provides definitive proof of the presence of a reducing sugar in the sample.

The method according to the invention may also include an additional step wherein the sample is pretreated with a glycosidase, such as invertase, prior to contacting the sample with the test reagent. This step allows nonreducing sugars, such as sucrose, to be converted into reducing forms capable of detection by the reducing sugar-specific indicator.

The invention also encompasses preparation of the test reagent by the addition of a material pre-absorbed with indicator to an aqueous solution thereby dissolving the indicator present in the pre-adsorbed material to form fresh test reagent. The indicator pre-adsorbed material offers the distinct advantage of maintaining the indicator in a dry, easily-stored form prior to carrying out the method.

Various other features, objects, and advantages of the invention will be made apparent to those skilled in the art from the following detailed description of the invention.

DETAILED DESCRIPTION OF THE INVENTION

In general, the invention disclosed herein may be used to detect the presence of sugars in samples. Appropriate samples may be liquid, solid or a combination of liquid and solid. An appropriate liquid may be a beverage item and an appropriate solid may be a food item.

Indicators useful with the present invention include compounds belonging generally to the phenazine class. Specifically, azocarmine B (1), indoine blue (2), methylene violet 3RAX (3), safranine O (4), phenosafronin (5), Janus Green B (6) and combinations thereof as shown below.

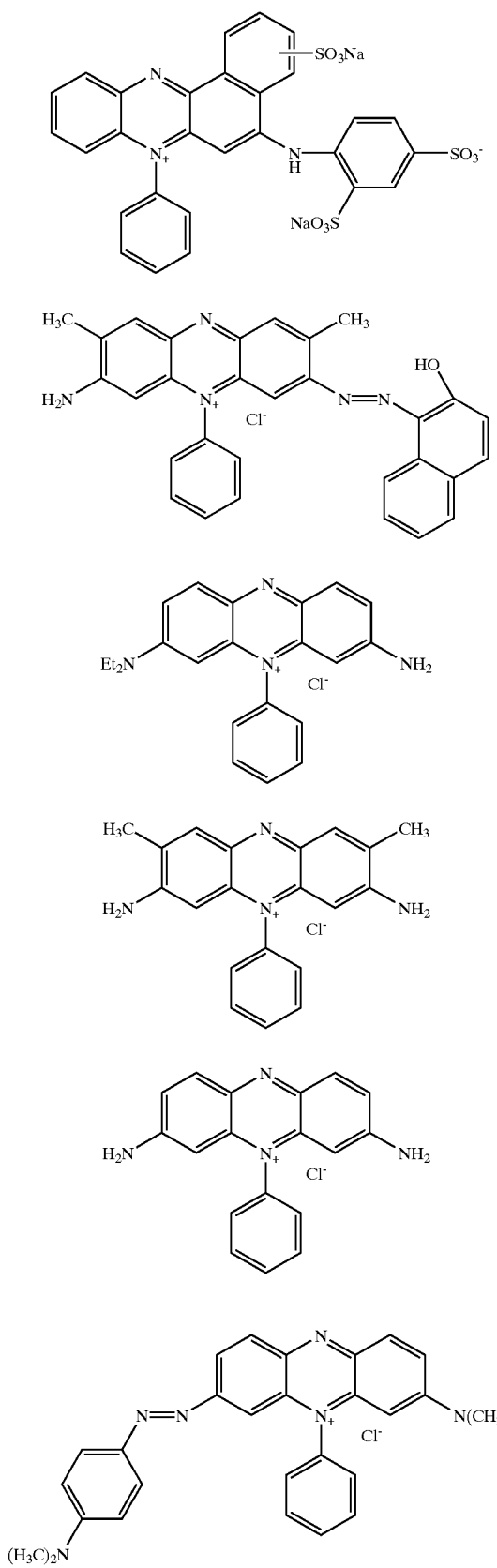

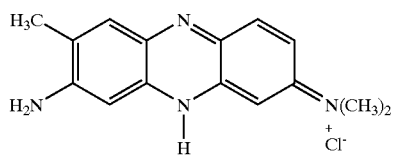

The preceding list is meant to be illustrative and not inclusive of all compounds from the phenazine class which are useful with the invention. However, not all phenazines are effective with the present invention. For instance, neutral red (7), shown above, fails to give a color change in the presence of reducing sugars. Compounds from other chemical classes, such as phenothiazine, phenoxazine, xanthine, acridine, anthraquinone, azo and sulfonephthalein classes, do not show the resistance to photodegradation exhibited by compounds within the phenazine class. Thus, compounds in the phenazine class are considered an improvement over non-phenazine compounds in regard to the present invention. Janus Green B is the preferred indicator for carrying out the invention.

The indicators useful in the invention are believed to undergo calorimetric changes visible to the naked eye in response to electron transfer reactions between the indicator and a reducing agent capable of donating electrons. The reducing agent is a reducing sugar in the case of the invention. As an example, blue-colored Janus Green B in alkaline media may be reversibly converted into a gray colored compound by an electron transfer from a reducing agent molecule to a Janus Green B molecule.

The term sugar, as used herein, includes both reducing and non-reducing sugars. A reducing sugar is defined as any sugar in which the carbonyl (anomeric) carbon is not involved in a glycosidic bond and can therefore undergo oxidation. Reducing sugars may include simple monosaccharides such as glucose, fructose, galactose, mannose and arabinose. Reducing sugar also encompasses homo- and heteropolysaccharides having a terminal sugar with a free anomeric carbon, thus allowing the terminal residue to act as a reducing residue.

Nonreducing sugars, as defined herein, are sugars lacking a free anomeric carbon. Such sugars do not bear a free carbonyl group capable of oxidation to a carboxylic acid. An example of a nonreducing sugar commonly found in food and beverage items is sucrose. Sucrose lacks a free carbonyl group capable of oxidation to a carboxylic acid. In order to detect nonreducing sugars in the present invention, an additional step of degrading the nonreducing sugar to subunits, some of which are reducing sugars, is included. Degradation of nonreducing sugars may be accomplished by enzymatic or chemical approaches in the present invention. For example, the enzyme invertase, a glycosidase, is useful to pretreat a sample suspected of containing sucrose in order to degrade sucrose to its glucose and fructose subunits, both of which are reducing sugars. Invertase is a specific example further illustrated below but other glycosidases capable of hydrolyzing bonds between sugar subunits are envisioned to be within the scope of the invention. Alternatively, a non-enzymatic approach to degradation of nonreducing sugars may be by acid hydrolysis, carried out by the simple acidification of a sample for a brief period prior to contact with the indicator.

The following is a description of the preferred method by which the invention may be carried out by a user. The method may be carried out in a reagent reservoir, or container, in which the reaction between a test reagent and any reducing sugar present in a sample can be visualized by a user. Such a container could be a vial, preferably a snap top vial constructed of polypropylene. Suitable snap top vials are available from Evergreen Scientific, 2300 East 49$^{th}$ Street, P.O. Box 58248, Los Angeles, Calif. 90058-0248. However, any container capable of containing the test reagent and suitable for providing a chamber in which contact of the test reagent and the food item is facilitated is suitable as long as the criteria set forth herein are satisfied. The container will be of a convenient size to carry or fit in a kit format, will include a reliable sealing enclosure, will have a construction not subject to decomposition by the alkaline test reagent (e.g.; polypropylene, polyethylene, polystyrene polymers), and will include a transparent or translucent portion for allowing a user to visually identify any calorimetric changes in the test reagent indicative of the presence of reducing sugars.

The preferred test reagent for carrying out the method contains 25 drops (approximately 0.45 mL) of a 0.4 N aqueous solution of NaOH (Aldrich Chemical Company, 1001 W. St. Paul Avenue, Milwaukee, Wis. 53233). As used herein, one drop is equal to approximately 0.018–0.020 mL. To this is added I drop of a 0.2% (w:w) aqueous solution of Janus Green B (Aldrich Chemical Company), (percentages throughout are weight:weight (w:w)). Alternatively, an indicator maybe not initially mixed with the 0.4 N NaOH solution during manufacture but the indicator, such as Janus Green B, may be adsorbed to an adsorbent material such as filter paper, cotton, or equivalent for addition to the NaOH solution immediately prior to carrying out the method. The adsorbent material pre-adsorbed with indicator at the equivalent of 1 drop of Janus Green B (0.2% w:w) may be placed into a snap top vial already containing the NaOH solution. The vial is then closed and briefly shaken to dissolve the Janus Green B into the NaOH solution thusly providing fresh test reagent. Although the phenazine class of compounds have been identified to provide enhanced stability and long term storage potential over and above other classes of compounds, use of pre-adsorbed indicator materials is envisioned to further improve the utility of the present invention.

To continue with the preferred embodiment of carrying out the invention, 5 drops of a liquid sample, such as a beverage, are added to the vial containing the test reagent and the snap top is closed. Alternatively, a solid food item approximating the volume of 5 drops may be added to the vial where a solid food item instead of a beverage is being tested. The small volume of liquid or solid sample utilized ensures that interference with the invention's colorimetric determination is minimized due to discoloring effects of food additives or dyes present in the sample. The vial is then inverted or shaken to uniformly mix the components.

Any color change in the test reagent is then observed after a brief and not inconvenient time period is allowed to pass. Depending upon the indicator used, this time period may range from less than 1 minute to approximately 15 minutes. Indicators having short time periods (1–2.5 minutes) are, of course, preferred to make the invention especially convenient for use. In addition, any color change observed in the method according to the invention may be compared with a standard solution included in the kit consisting of the test reagent alone to which five drops of water have been added so that any ambiguity is removed from the calorimetric determination by providing a comparative standard.

The following examples further illustrate the advantages of the present invention for the detection of sugars in samples.

EXAMPLE 1.

This example demonstrates the effect of phenazine compound concentration on colorimetric test results using a known reducing sugar, fructose, as a positive control.

Two milliliter (mL) polypropylene tubes were prepared to which 25 drops of a 0.4 N KOH solution were added. To each tube was added one of the following compounds shown in the first column of Table 1. The second column of Table 1 indicates the initial concentration of the compounds and how many drops of the compound were added to the KOH solution to form a test reagent.

Following formation of the test reagent, 5 drops of a 10% (w/w) aqueous solution of fructose (positive control) was added to each of the test reagents. The third column of Table 1 indicates the initial color of the test reagent before addition of the fructose solution and the fourth column indicates the final color of the solution after addition of the fructose solution. The fifth column of Table 1 indicates the time between addition of the fructose solution and the time the final color was achieved.

TABLE 1

| Dye | Concentration (# of drops) | Initial Color | Final Color | Time until color change* |
|---|---|---|---|---|
| Azocarmine B | 0.01% (3) | Light Pink | Light Pink | — |
| Azocarmine B | 0.10% (1) | Pink | Pink | — |
| Indoine Blue | 0.01% (10) | Light Violet | Light Blue | 3 min 30 sec |
| Indoine Blue | 0.10% (2) | Violet | Blue | 3 minutes |
| Janus Green B | 0.01% (3) | Light Blue | Light Grey | 30 seconds |
| Janus Green B | 0.01% (1) | Blue | Grey | 30 seconds |
| Me. Violet3RAX | 0.01% (1) | Light Violet | Colorless | 1 min 45 sec |
| Me. Violet3RAX | 0.10% (1) | Violet | Colorless | 1 min 40 sec |
| Neutral Red | 0.10% (1) | Light Orange | Light Orange | — |
| Phenosafranin | 0.01% (1) | Pink | Colorless | 1 min 13 sec |
| Phenosafranin | 0.10% (1) | Red | Colorless | 1 min 8 sec |
| Safranine O | 0.01% (2) | Light Pink | Colorless | 1 min 35 sec |
| Safranine O | 0.10% (1) | Pink | Colorless | 1 min 45 sec |
| Methylene Blue | 0.01% (1) | Light Blue | Colorless | 25 seconds |
| Methylene Blue | 0.10% (1) | Blue | Colorless | 27 seconds |

*A dash indicates no change in color after 1 hour.

EXAMPLE 2.

This example demonstrates the effect of base and base concentration on colorimetric test results for a group of phenazine compounds. As in the preceding example, polypropylene tubes were prepared to which 25 drops of base solution were added as indicated in the second column of Table 2. The initial concentration of the base is also indicated in the second column of Table 2. To each tube containing a respective base solution, one drop of 0.1% (w/w) of phenazine compound was added as indicated in column 1 of Table 2. Subsequently, 5 drops of 10% (w/w) fructose solution was added to the dye/base combination. The third column of Table 2 indicates the initial color of the base/dye combination. The fourth column of Table 2 indicates the final color of the solution after addition of the fructose solution. The fifth and final column of Table 2 indicates the time necessary for each of the respective reactions to achieve the final color noted in column 4.

TABLE 2

| Dye | Base Concentration | Initial Color | Final Color | Time until color change** |
|---|---|---|---|---|
| Janus Green B | KOH (0.4 N) | Blue | Grey | 29 seconds |
| Janus Green B | KOH (0.1 N) | Blue | Grey | 1 min 55 sec |
| Janus Green B | $K_2CO_3$ (0.4 N) | Blue | Blue | — |
| Janus Green B | NaOH (4.0 N) | Violet | Grey | 6 seconds |
| Janus Green B | NaOH (0.4 N) | Blue | Grey | 13 seconds |
| Janus Green B | NaOH (0.1 N) | Blue | Grey | 33 seconds |
| Janus Green B | NaOH (0.04 N) | Blue | Grey | 1 min 28 sec |
| Janus Green B | $NH_4OH$ (8.0 N) | Blue | Grey | 3 min 30 sec |
| Janus Green B | $NH_4OH$ (2.0 N) | Blue | Grey | 9 min 40 sec |
| Janus Green B | $Ba(OH)_2$ (0.4 N) | Blue | Grey | 29 seconds |
| Janus Green B | $Ba(OH)_2$ (0.1 N) | Blue | Grey | 38 seconds |
| Janus Green B | $Sr(OH)_2$ (0.4 N) | Blue | Grey | 28 seconds |
| Phenosafranin | KOH (0.4 N) | Pink | Colorless | 1 min 10 sec |
| Phenosafranin | KOH (0.1 N) | Pink | Pink | — |
| Phenosafranin | $K_2CO_3$ (0.4 N) | Pink | Pink | — |
| Phenosafranin | NaOH (4.0 N) | Red Violet | Colorless | 9 seconds |
| Phenosafranin | NaOH (0.4 N) | Pink | Colorless | 28 seconds |
| Phenosafranin | NaOH (0.1 N) | Pink | Colorless | 3 min 20 sec |
| Phenosafranin | NaOH (0.04 N) | Pink | Colorless | 50 minutes |
| Phenosafranin | NaOH (8.0 N) | Pink | Pink | — |
| Phenosafranin | $NH_4OH$ (2.0 N) | Pink | Pink | — |
| Phenosafranin | $Ba(OH)_2$ (0.4 N) | Pink | Colorless | 51 seconds |
| Phenosafranin | $Ba(OH)_2$ (0.1 N) | Pink | Colorless | 1 min 55 sec |
| Phenosafranin | $Sr(OH)_2$ (0.4 N) | Pink | Colorless | 1 min 7 sec |

**A dash indicates no change in color after 1 hour.

EXAMPLE 3.

This example is directed to the effect of various solvents on the detection of reducing sugars by the present invention. The phenazine compounds indicated in column 1 of Table 3 below were initially dissolved in the indicated solvent to an initial concentration of 0.1% (w/w). One drop of this standard solution was then added to 25 drops of the base/solvent combination indicated in column 2. KOH was the base used in this example and was dissolved at a concentration of 0.4N in the respective solvent. To each of the respective test reagents was added 5 drops of 10% (w/w) fructose. Column 3 of Table 3 indicates the initial color of the test reagent before addition of the fructose solution. Column 4 of Table 3 indicates the final color of the test reagent following addition of the fructose solution and column 5 indicates the time necessary for the solution to achieve its final color.

TABLE 3

| Dye | Base/Solvent | Initial Color | Final Color | Time |
|---|---|---|---|---|
| Janus Green B | KOH/MeOH | Blue | Grey | 10 seconds |
| Phenosafranin | KOH/MeOH | Pink | Colorless | 53 seconds |
| Methylene Blue | KOH/MeOH | Turquoise Blue | Pale Pink | 21 seconds |
| Janus Green B | KOH/EtOH | Blue | Abt. Colorless | 58 seconds |
| Phenosafranin | KOH/EtOH | Pink | Colorless | 35 seconds |
| Methylene Blue | KOH/EtOH | Blue | Colorless | 30 seconds |
| Janus Green B | KOH/I-PrOH | Blue | Grey | 9 seconds |
| Phenosafranin | KOH/I-PrOH | Pink | Colorless | 1 min 15 sec |
| Methylene Blue | KOH/I-PrOH | Grey Blue | Colorless | 45 seconds |
| Janus Green B | KOH/t-BuOH | Blue | Grey | 4 minutes |
| Phenosafranin | KOH/t-BuOH | Pink | Lighter Pink | 15 minutes |
| Methylene Blue | KOH/t-BuOH | Blue | Violet | 1 min 25 sec |
| Janus Green B | KOH/glycerol | Blue | Grey | 10 seconds |
| Phenosafranin | KOH/glycerol | Deep Pink | Pale Pink | 4 min 30 sec |

For all data in this example, dye concentration was 0.1% w/w in the solvent shown and KOH concentration was 0.4 N.

EXAMPLE 4.

This example illustrates the utility of the present invention with a variety of reducing sugar-containing liquids. Individual tests were carried out substantially as described for the previous examples. The phenazine compound indicated in column 2 of Table 4 was dissolved to initially form a 0.1% (w/w) aqueous stock solution. Unless indicated otherwise, one drop of this stock solution was then added to 25 drops of the base solution indicated in column 3 of Table 4. Subsequently, 5 drops of the test solution indicated in column 1 of Table 4 were added to the test reagent and the time to a definitive color change was recorded and is indicated in column 4 of Table 4.

TABLE 4

| Test Solution | Dye | Base | Color Change Time** |
|---|---|---|---|
| 10% Fructose | Janus Green B | 0.4 N KOH | 15 seconds |
| 10% Fructose | Phenosafranin | 0.4 N KOH | 1 minute, 5 seconds |
| 10% Fructose | Janus Green B | 0.4 N $Ba(OH)_2$ | 15 seconds |
| 10% Fructose | Phenosafranin | 0.4 N $Ba(OH)_2$ | 3 minutes, 20 seconds |
| 10% Fructose | Janus Green B | 0.4 N NaOH | 13 seconds |
| 10% Fructose | Phenosafranin | 0.4 N NaOH | 28 seconds |
| 10% Glucose | Janus Green B | 0.4 N KOH | 4 minutes, 45 seconds |
| 10% Glucose | Phenosafranin | 0.4 N KOH | 7 minutes, 40 seconds |
| 10% Glucose | Janus Green B | 0.4 N $Ba(OH)_2$ | 2 minutes, 20 seconds |
| 10% Glucose | Phenosafranin | 0.4 N $Ba(OH)_2$ | 3 minutes, 20 seconds |
| 10% Glucose | Janus Green B | 0.4 N NaOH | 1 minute, 25 seconds |
| 10% Glucose | Phenosafranin | 0.4 N NaOH | 4 minutes, 10 seconds |
| 10% Corn Syrup | Janus Green B | 0.4 N KOH | 5 minutes, 45 seconds |
| 10% Corn Syrup | Phenosafranin | 0.4 N KOH | 13 minutes, 30 seconds |
| 10% Corn Syrup | Janus Green B | 0.4 N $Ba(OH)_2$ | 2 minutes, 10 seconds |
| 10% Corn Syrup | Phenosafranin | 0.4 N $Ba(OH)_2$ | 2 minutes, 45 seconds |
| 10% Corn Syrup | Janus Green B | 0.4 N NaOH | 3 minutes |
| 10% Corn Syrup | Phenosafranin | 0.4 N NaOH | 12 minutes, 30 seconds |
| 10% Honey | Janus Green B | 0.4 N KOH | 1 minute, 50 seconds |
| 10% Honey | Phenosafranin | 0.4 N KOH | 2 minutes, 50 seconds |
| 10% Honey | Janus Green B | 0.4 N $Ba(OH)_2$ | 35 seconds |
| 10% Honey | Phenosafranin | 0.4 N $Ba(OH)_2$ | 1 minute, 5 seconds |
| 10% Honey | Janus Green B | 0.4 N NaOH | 45 seconds |
| 10% Honey | Phenosafranin | 0.4 N NaOH | 2 minutes, 10 seconds |
| 10% Molasses | Janus Green B | 0.4 N KOH | 30 seconds |
| 10% Molasses | Phenosafranin | 0.4 N KOH | 2 minutes, 30 seconds |
| 10% Molasses | Janus Green B | 0.4 N $Ba(OH)_2$ | 10 seconds |
| 10% Molasses | Phenosafranin | 0.4 N $Ba(OH)_2$ | 30 seconds |
| 10% Molasses | Janus Green B | 0.4 N NaOH | 35 seconds |
| 10% Molasses | Phenosafranin | 0.4 N NaOH | 1 minute, 25 seconds |
| Pineapple Juice | Janus Green B | 0.4 N KOH | 35 seconds |
| Pineapple Juice | Phenosofranin | 0.4 N KOH | 40 seconds |
| Pineapple Juice | Janus Green B | 0.4 N $Ba(OH)_2$ | 9 seconds |
| Pineapple Juice | Phenosafranin | 0.4 N $Ba(OH)_2$ | 13 seconds |
| Pineapple Juice | Janus Green B | 0.4N NaOH | 40 seconds |
| Pineapple Juice | Phenosafranin | 0.4 N NaOH | 1 minute, 10 seconds |
| Orange Juice | Janus Green B | 0.4 N KOH | 25 seconds |
| Orange Juice | Phenosafranin | 0.4 N KOH | 1 minute, 58 seconds |
| Orange Juice | Janus Green B | 0.4 N $Ba(OH)_2$ | 25 seconds |
| Orange Juice | Phenosafranin | 0.4 N $Ba(OH)_2$ | 35 seconds |
| Orange Juice | Janus Green B | 0.4 N NaOH | 20 seconds |
| Orange Juice | Phenosafranin | 0.4 N NaOH | 1 minute, 50 seconds |
| Cranberry Juice | Janus Green B | 0.4 N KOH | 15 seconds |
| Cranberry Juice | Phenosafranin | 0.4 N KOH | 50 seconds |
| Cranberry Juice | Janus Green B | 0.4 N $Ba(OH)_2$ | 7 seconds |
| Cranberry Juice | Phenosafranin | 0.4 N $Ba(OH)_2$ | 20 seconds |
| Cranberry Juice | Janus Green B | 0.4 N NaOH | 15 minutes |
| Cranberry Juice | Phenosafranin | 0.4 N NaOH | 35 seconds |
| Lemon Juice | Janus Green B | 0.4 N KOH | 55 seconds |
| Lemon Juice | Phenosafranin | 0.4 N KOH | >15 minutes |
| Lemon Juice | Janus Green B | 0.4 N $Ba(OH)_2$ | 20 seconds (ppt. formed) |
| Lemon Juice | Phenosafranin | 0.4 N $Ba(OH)_2$ | >15 minutes (ppt.) |
| Lemon Juice | Janus Green B | 0.4 N NaOH | 1 minute, 45 seconds |

TABLE 4-continued

| Test Solution | Dye | Base | Color Change Time** |
|---|---|---|---|
| Lemon Juice | Phenosafranin | 0.4 N NaOH | 5 minutes, 30 seconds |
| Lime Juice | Janus Green B | 0.4 N KOH | 4 minutes, 45 seconds |
| Lime Juice | Phenosafranin | 0.4 N KOH | >15 minutes |
| Lime Juice | Janus Green B | 0.4 N Ba(OH)$_2$ | 1 minute, 30 sec. (ppt.) |
| Lime Juice | Phenosafranin | 0.4 N Ba(OH)$_2$ | >15 minutes (ppt.) |
| Lime Juice | Janus Green B | 0.4 N NaOH | 1 minute, 40 seconds |
| Lime Juice | Phenosafranin | 0.4 N NaOH | 5 minutes, 30 seconds |
| Coca Cola (Classic) | Janus Green B | 0.4 N KOH | 1 minute, 5 seconds |
| Coca Cola (Classic) | Phenosafranin | 0.4 N KOH | 1 minute, 40 seconds |
| Coca Cola (Classic) | Janus Green B | 0.4 N Ba(OH)$_2$ | 15 seconds (ppt.) |
| Coca Cola (Classic) | Phenosafranin | 0.4 N Ba(OH)$_2$ | 38 seconds (ppt.) |
| Coca Cola (Classic) | Janus Green B | 0.4 N NaOH | 25 seconds |
| Coca Cola (Classic) | Phenosafranin | 0.4 N NaOH | 2 minutes, 10 seconds |
| Coca Cola (Diet) | Janus Green B | 0.4 N KOH | — |
| Coca Cola (Diet) | Phenosafranin | 0.4 N KOH | — |
| Coca Cola (Diet) | Janus Green B | 0.4 N Ba(OH)$_2$ | — (ppt.) |
| Coca Cola (Diet) | Phenosafranin | 0.4 N Ba(OH)$_2$ | — (ppt.) |
| Coca Cola (Diet) | Janus Green B | 0.4 N NaOH | — |
| Coca Cola (Diet) | Phenosafranin | 0.4 N NaOH | — |
| White Wine | Janus Green B | 0.4 N KOH | 2 minutes, 10 seconds |
| White Wine | Phenosafranin | 0.4 N KOH | 5 minutes, 45 seconds |
| White Wine | Janus Green B | 0.4 N Ba(OH)$_2$ | 35 seconds |
| White Wine | Phenosafranin | 0.4 N Ba(OH)$_2$ | 1 minute, 20 seconds |
| White Wine | Janus Green B | 0.4 N NaOH | 1 minute, 5 seconds |
| White Wine | Phenosafranin | 0.4 N NaOH | 3 minutes, 15 seconds |

** A dash indicates no change in color after 1 hour.

Test solutions identified in Table 4 were available from the following sources: 10% aqueous solution of glucose (positive control; available from Aldrich Chemical Company); 10% aqueous solution of fructose (positive control; available from Aldrich Chemical Company); 10% aqueous solution of sucrose (negative control; available from Aldrich Chemical Company); a carbonated beverage (available from the CCE Bottling Group, Atlanta, Georgia, canned by authority of the Coca-Cola Company, Atlanta, Georgia under the registered trademark CLASSIC COCA COLA); a carbonated diet beverage (available from the CCE Bottling Group, Atlanta, Georgia, canned by authority of the Coca-Cola Company, Atlanta, Georgia under the registered trademark DIET COCA COLA); white wine (available from Ferdinand Pieroth, GMBH, Germany under the registered trademark PEIROTH BLUE, 1990 Burg Layer Schlosskapelle Kabinett Nahe); 10% aqueous solution of honey (premium clover honey available from Sioux Honey Association, Sioux City, Iowa under the trademark SUE BEE); 10% aqueous solution of molasses (an unsulfured molasses available from Mott's USA, a division of Cadbury Beverages, Inc., Stanford, Connecticut under the registered trademark GRANDMA'S MOLASSES); 10% aqueous solution of corn syrup (available from BestFoods, Englewood Cliffs, N.J. under the registered trademark KARO'S CORN SYRUP); pineapple juice available from Dole Juice Co., Brandenton, Fla. 34206 under the registered trademark DOLE 100% Juice Pineapple Juice; orange juice available from American Procurement and Logistics Co., P.O. Box 27447, Salt Lake City, Utah 84127-0447 under the registered trademark JEWEL; cranberry juice available from Ocean Spray Cranberries, Inc., Lakeville-Middleboro, Mass. 02349, under the registered trademark OCEAN SPRAY Cranberry Juice Cocktail; lemon juice available from Eagle Family Foods, Inc., Tarrytown, N.Y. 10591 under the registered trademark REALEMON Lemon Juice; and lime juice available from Eagle Family Foods Inc., Tarrytown, N.Y. 10591 under the registered trademark REALIME Lime Juice.

EXAMPLE 5.

The sweetener in many food and beverage items is occasionally not a reducing sugar such as glucose or fructose but a nonreducing sugar such as the disaccharide sucrose. In order to show that the detection of nonreducing sugars is encompassed within the invention, the following example was created. A suspension of 10 milligrams (mg) of a crude commercial invertase (53 Units/mg solid; available from Sigma-Aldrich, Inc., Grade V, Practical, from Baker's Yeast; units are defined as the quality of invertase that will hydrolyze 1.0 μmole of sucrose to invert sugar per minute at pH 4.5 at 55° C. in 1.0 mL water) was prepared with mixing and the insoluble solids were allowed to settle, after which the supernatant was drawn off. To 40 drops of an aqueous 10% sucrose solution was added 5 drops of the invertase supernatant. The mixture was allowed to stand for 3 minutes, after which 5–10 drops of the resulting sucrose solution was added to tubes containing indicators (see Table 5 below), as prepared in Example 1, above.

Concentrations on the order of 20–25 mg/mL of invertase (approximately 1,000 units/mL) are useful in the invention. Lower concentrations of invertase may be utilized, but much longer incubation times will be required to produce sufficient reducing sugar to decolorize the test reagent in a reasonable period of time.

TABLE 5

| Test Solution | Dye | Base | Color Change Time** |
|---|---|---|---|
| 10% Sucrose | Janus Green B | 0.4 N KOH | — |
| 10% Sucrose | Phenosafranin | 0.4 N KOH | — |
| 10% Sucrose | Janus Green B | 0.4 N Ba(OH)$_2$ | — |
| 10% Sucrose | Phenosafranin | 0.4 N Ba(OH)$_2$ | — |
| 10% Sucrose | Janus Green B | 0.4 N NaOH | — |
| 10% Sucrose | Phenosafranin | 0.4 N NaOH | — |
| 10% Suc. 0.1% Invert. | Janus Green B | 0.4 N KOH | 2 minutes, 30 seconds |
| 10% Suc. 0.1% Invert. | Phenosafranin | 0.4 N KOH | 14 minutes, 30 seconds |
| 10% Suc. 0.1% Invert. | Janus Green B | 0.4 N Ba(OH)$_2$ | 1 minute, 45 seconds |
| 10% Suc. 0.1% Invert. | Phenosafranin | 0.4 N Ba(OH)$_2$ | 3 minutes |
| 10% Suc. 0.1% Invert. | Janus Green B | 0.4 N NaOH | 1 minute, 40 seconds |
| 10% Suc. 0.1% Invert. | Phenosafranin | 0.4 N NaOH | 13 minutes |
| 10% Suc. 0.5% Invert. | Janus Green B | 0.4 N KOH | 2 minutes, 15 seconds |
| 10% Sec. 0.5% Invert. | Phenosafranin | 0.4 N KOH | 6 minutes |
| 10% Suc. 0.5% Invert. | Janus Green B | 0.4 N Ba(OH)$_2$ | 1 minute, 30 seconds |
| 10% Suc. 0.5% Invert. | Phenosafranin | 0.4 N Ba(OH)$_2$ | 2 minutes |
| 10% Suc. 0.5% Invert. | Janus Green B | 0.4 N NaOH | 45 seconds |
| 10% Suc. 0.5% Invert. | Phenosafranin | 0.4 N NaOH | 8 minutes, 30 seconds |

**A dash indicates no change in color after 1 hour.

EXAMPLE 6.

The present invention is practiced with test reagents prepared with indicators from the phenazine class of compounds. These particular compounds have been shown to possess improved resistance to photodegradation in comparison to previously known indicator compounds. For example, alkaline 0.1% (w/w) methylene blue aqueous solutions, placed under a florescent ceiling light at a distance of approximately 5 feet, are photobleached from a blue to a colorless state after approximately 2.5 minutes. However, Janus Green B prepared in exactly the same manner and placed under similar lighting conditions is still colored and usable in the present invention after several hours. In direct sunlight, alkaline 0.1% methylene blue was photobleached within 30 seconds to an unusable compound. In comparison, alkaline 0.1% Janus Green B was not appreciably photobleached even after 15 minutes in direct sunlight. In addition, it has also been shown that alkaline 0.1% Janus Green B solutions may be stored at 0° C. in the dark and still be usable after one month of storage.

While the invention has been described with reference to preferred embodiments, those skilled in the art will appreciate that certain substitutions, alterations, and omissions may be made without departing from the spirit of the invention. Accordingly, the foregoing description is meant to be exemplary only and should not limit the scope of the invention set forth in the following claims.

What is claimed is:

1. A method of detecting reducing sugars in a sample comprising the steps of:
    contacting a test reagent with the sample, the test reagent having an alkaline pH and including an indicator capable of providing a colorimetric change when contacted with reducing sugar in the sample;
    subsequently detecting a colorimetric change in the indicator indicating the presence of reducing sugars in the sample.

2. A method according to claim 1 wherein the indicator is a phenazine compound.

3. A method according to claim 2 wherein the phenazine compound selected from the group consisting of azocarmine B, indoine blue, methylene violet 3RAX, safranine O, phenosafranin, and Janus Green B.

4. A method according to claim 1 wherein the test reagent further comprises a base selected from the group consisting of NaOH, KOH, $Sr(OH)_2$, $Ba(OH)_2$, and $NH_4OH$.

5. A method according to claim 1 including the additional step of pretreating the sample with a glycosidase prior to contacting the sample with the test reagent.

6. A method according to claim 5 wherein the glycosidase is invertase.

7. A method according to claim 1 wherein the indicator is pre-adsorbed onto an adsorbent material to form a pre-adsorbed material and the pre-adsorbed material is added to an alkaline solution to generate the test reagent prior to contacting the test reagent with the sample.

8. A method of detecting reducing sugars in a sample comprising the steps of
    contacting a test reagent with the sample, the test reagent having an alkaline pH and including a phenazine compound capable of providing a calorimetric change when contacted with reducing sugar in the sample;
    subsequently detecting a calorimetric change in the phenazine compound indicating the presence of reducing sugars in the sample.

9. A method of detecting reducing sugars in a sample comprising the steps of:
    contacting a test reagent with the sample, the test reagent having an alkaline pH and including an indicator selected from the group consisting of azocarmine B, indoine blue, methylene violet 3 RAX, safranine O, phenosafranine, and Janus Green B, the indicator capable of providing a calorimetric change when contacted with reducing sugar in the sample;
    subsequently detecting a colorimetric change in the indicator indicating the presence of reducing sugars in the sample.

10. A method of detecting sugars comprising the steps of:
    pretreating the sample with a glycosidase to form a pretreated sample;
    contacting a test reagent with the pretreated sample, the test reagent having an alkaline pH and including a phenazine compound capable of providing a calorimetric change when contracted with reducing sugar within the sample;
    subsequently detecting a colorimetric change in the indicator indicating the presence of reducing sugars in the sample.

* * * * *